US009949649B2

(12) United States Patent
 Takei et al.

(10) Patent No.: US 9,949,649 B2
(45) Date of Patent: Apr. 24, 2018

(54) BIOLOGICAL INFORMATION MEASUREMENT DEVICE

(71) Applicant: Seiko Epson Corporation, Shinjuku-ku (JP)

(72) Inventors: Yukio Takei, Shiojiri (JP); Takeshi Mochimaru, Chino (JP); Takahiro Kamijo, Fujimi-machi (JP)

(73) Assignee: Seiko Epson Corporation, Tokyo (JP)

( * ) Notice: Subject to any disclaimer, the term of this patent is extended or adjusted under 35 U.S.C. 154(b) by 602 days.

(21) Appl. No.: 14/512,272

(22) Filed: Oct. 10, 2014

(65) Prior Publication Data

US 2015/0105678 A1    Apr. 16, 2015

(30) Foreign Application Priority Data

Oct. 11, 2013  (JP) ................................. 2013-213480

(51) Int. Cl.
 *A61B 5/00*   (2006.01)
 *A61B 5/024*  (2006.01)
 *G04G 21/02*  (2010.01)

(52) U.S. Cl.
 CPC ............ *A61B 5/02438* (2013.01); *A61B 5/00* (2013.01); *A61B 5/681* (2013.01); *A61B 5/7285* (2013.01); *G04G 21/025* (2013.01); *A61B 5/024* (2013.01); *A61B 2560/0209* (2013.01); *A61B 2560/0214* (2013.01)

(58) Field of Classification Search
 CPC .... A61B 2560/0209; A61B 2560/0214; A61B 5/00; A61B 5/024; A61B 5/02438; A61B 5/681; A61B 5/7285; G04G 21/025

USPC ................................. 600/500–503, 481, 483
See application file for complete search history.

(56) References Cited

U.S. PATENT DOCUMENTS

| 6,553,242 | B1 * | 4/2003 | Sarussi | A61B 5/0261 |
| | | | | 600/323 |
| 6,697,658 | B2 * | 2/2004 | Al-Ali | A61B 5/1455 |
| | | | | 600/323 |
| 7,171,251 | B2 * | 1/2007 | Sarussi | A61B 5/02433 |
| | | | | 600/324 |
| 7,507,207 | B2 * | 3/2009 | Sakai | A61B 5/02438 |
| | | | | 600/300 |

(Continued)

FOREIGN PATENT DOCUMENTS

| EP | 1421896 A2 | 5/2004 |
| EP | 1421896 A3 | 8/2004 |

(Continued)

OTHER PUBLICATIONS

Extended European Search Report, dated Apr. 23, 2015, of the corresponding European Application No. 14188087.2; 14 pages.

(Continued)

*Primary Examiner* — Navin Natnithithadha
(74) *Attorney, Agent, or Firm* — Kilpatrick Townsend & Stockton LLP

(57) ABSTRACT

A biological information measurement device includes a device main body which includes a sensor, a processor, and a battery. The sensor acquires biological information of a user. The processor instructs the sensor to acquire the information at certain discrete times with a period, and processes the information. The battery supplies power to the sensor and the processor. The period is selected based on the biological information.

13 Claims, 7 Drawing Sheets

(56) References Cited

U.S. PATENT DOCUMENTS

| | | | |
|---|---|---|---|
| 7,590,438 B2 * | 9/2009 | Sarussi | A61B 5/02433 600/324 |
| 7,603,152 B2 * | 10/2009 | Sarussi | A61B 5/02433 600/324 |
| 7,606,607 B2 * | 10/2009 | Sarussi | A61B 5/02433 600/324 |
| 7,613,490 B2 * | 11/2009 | Sarussi | A61B 5/02433 600/324 |
| 7,650,176 B2 * | 1/2010 | Sarussi | A61B 5/02433 600/324 |
| 8,734,296 B1 * | 5/2014 | Brumback | G06F 19/3406 482/8 |
| 8,784,271 B2 * | 7/2014 | Brumback | 340/870.16 |
| 8,814,754 B2 | 8/2014 | Weast et al. | |
| 8,903,671 B2 * | 12/2014 | Park | G08B 21/18 702/104 |
| 8,944,958 B1 * | 2/2015 | Brumback | G06F 19/3406 482/8 |
| 8,974,349 B2 | 3/2015 | Weast et al. | |
| 8,988,214 B2 | 3/2015 | Altman et al. | |
| 9,011,292 B2 | 4/2015 | Weast et al. | |
| 9,026,927 B2 | 5/2015 | Brumback et al. | |
| 9,044,136 B2 | 6/2015 | Luo | |
| 9,113,841 B2 | 8/2015 | Amagai | |
| 9,141,087 B2 | 9/2015 | Brown et al. | |
| 9,141,759 B2 | 9/2015 | Burich et al. | |
| 9,160,063 B2 * | 10/2015 | Lowe, Jr. | G08C 19/16 |
| 9,317,660 B2 | 4/2016 | Burich et al. | |
| 9,352,207 B2 | 5/2016 | Balakrishnan et al. | |
| 9,474,955 B2 | 10/2016 | Cobbett et al. | |
| 9,504,414 B2 | 11/2016 | Coza et al. | |
| 9,533,228 B2 | 1/2017 | Dugan | |
| 2001/0024949 A1 | 9/2001 | Yanagida et al. | |
| 2003/0158692 A1 * | 8/2003 | Tamada | G06F 3/011 702/127 |
| 2003/0229276 A1 * | 12/2003 | Sarussi | A61B 5/02433 600/322 |
| 2007/0149871 A1 * | 6/2007 | Sarussi | A61B 5/02433 600/324 |
| 2007/0293746 A1 * | 12/2007 | Sarussi | A61B 5/02433 600/330 |
| 2008/0076988 A1 * | 3/2008 | Sarussi | A61B 5/02433 600/323 |
| 2008/0076990 A1 * | 3/2008 | Sarussi | A61B 5/02433 600/324 |
| 2008/0097228 A1 * | 4/2008 | Aihara | A61B 5/02116 600/490 |
| 2009/0040231 A1 * | 2/2009 | Sano | G06T 13/40 345/474 |
| 2009/0247849 A1 * | 10/2009 | McCutcheon | A61B 5/14551 600/323 |
| 2010/0217099 A1 * | 8/2010 | LeBoeuf | A61B 5/00 600/301 |
| 2010/0244574 A1 * | 9/2010 | Nishino | A61B 6/00 307/80 |
| 2010/0331145 A1 * | 12/2010 | Lakovic | G04F 10/00 482/8 |
| 2011/0125037 A1 * | 5/2011 | Iijima | A61B 5/681 600/500 |
| 2011/0213217 A1 * | 9/2011 | McKenna | A61B 5/14552 600/301 |
| 2012/0083671 A1 | 4/2012 | Kato et al. | |
| 2012/0083674 A1 | 4/2012 | Hidai et al. | |
| 2012/0253484 A1 | 10/2012 | Burich et al. | |
| 2012/0253485 A1 | 10/2012 | Weast et al. | |
| 2012/0254934 A1 | 10/2012 | McBrearty et al. | |
| 2012/0274508 A1 | 11/2012 | Brown et al. | |
| 2013/0041590 A1 | 2/2013 | Burich et al. | |
| 2013/0053697 A1 * | 2/2013 | Holl | A61B 8/54 600/459 |
| 2013/0106603 A1 | 5/2013 | Weast et al. | |
| 2013/0106684 A1 | 5/2013 | Weast et al. | |
| 2013/0110264 A1 | 5/2013 | Weast et al. | |
| 2013/0178750 A1 * | 7/2013 | Sheehan | A61F 2/2403 600/486 |
| 2013/0190908 A1 | 7/2013 | Ellis et al. | |
| 2013/0196688 A1 | 8/2013 | Lu et al. | |
| 2013/0197680 A1 | 8/2013 | Cobbett et al. | |
| 2013/0197857 A1 | 8/2013 | Lu et al. | |
| 2013/0217979 A1 | 8/2013 | Blackadar et al. | |
| 2013/0246021 A1 | 9/2013 | Ura et al. | |
| 2013/0274587 A1 | 10/2013 | Coza et al. | |
| 2013/0274904 A1 | 10/2013 | Coza et al. | |
| 2014/0077945 A1 | 3/2014 | Amagai | |
| 2014/0172132 A1 | 6/2014 | Ura | |
| 2014/0176335 A1 | 6/2014 | Brumback et al. | |
| 2014/0176346 A1 | 6/2014 | Brumback et al. | |
| 2014/0176422 A1 | 6/2014 | Brumback et al. | |
| 2014/0180595 A1 | 6/2014 | Brumback et al. | |
| 2014/0244009 A1 | 8/2014 | Mestas | |
| 2014/0306884 A1 | 10/2014 | Sano et al. | |
| 2014/0336519 A1 * | 11/2014 | Kaib | A61B 5/0006 600/515 |
| 2015/0031963 A1 * | 1/2015 | Wright | A61B 5/4238 600/301 |

FOREIGN PATENT DOCUMENTS

| | | | |
|---|---|---|---|
| JP | 2001-356849 A | 12/2001 | |
| JP | 2008-251073 A | 10/2008 | |
| JP | 2009-039157 A | 2/2009 | |
| JP | 2011-036617 A | 2/2011 | |
| JP | 2011-104234 A | 6/2011 | |
| JP | 2012-075489 A | 4/2012 | |
| JP | 2012-090975 A | 5/2012 | |
| JP | 2013-111202 A | 6/2013 | |
| WO | 2006-038628 A1 | 4/2006 | |
| WO | 2012/008264 A1 | 1/2012 | |

OTHER PUBLICATIONS

Extended European search report, dated Mar. 9, 2015, of the corresponding European Application No. 14188287.8; 9 pgs.

Narayanaswami, Chandra, et al, "Challenges and considerations for the design and production of a purpose-optimized body-worn wrist watch computer," Proceedings of SPIE, vol. 5443, Sep. 15, 2004, pp. 1-12.

Kamijoh, Noboru, et al., "Energy trade-offs in the IBM Wristwatch computer," Wearable Computers, 2001; Proceedings. Fifth International Symposium 0 N Oct. 8-9, 2001; Piscataway, NJ, USA; IEEE, Oct. 8, 2001, pp. 133-140.

Non-Final Office Action in related U.S. Appl. No. 14/511,605, dated Feb. 7, 2017 (22 pages).

Final Office Action in related U.S. Appl. No. 14/511,605, dated Aug. 15, 2017 (17 pages).

Non-Final Office Action in related U.S. Appl. No. 14/511,605, dated Dec. 12, 2017 (29 pages).

* cited by examiner

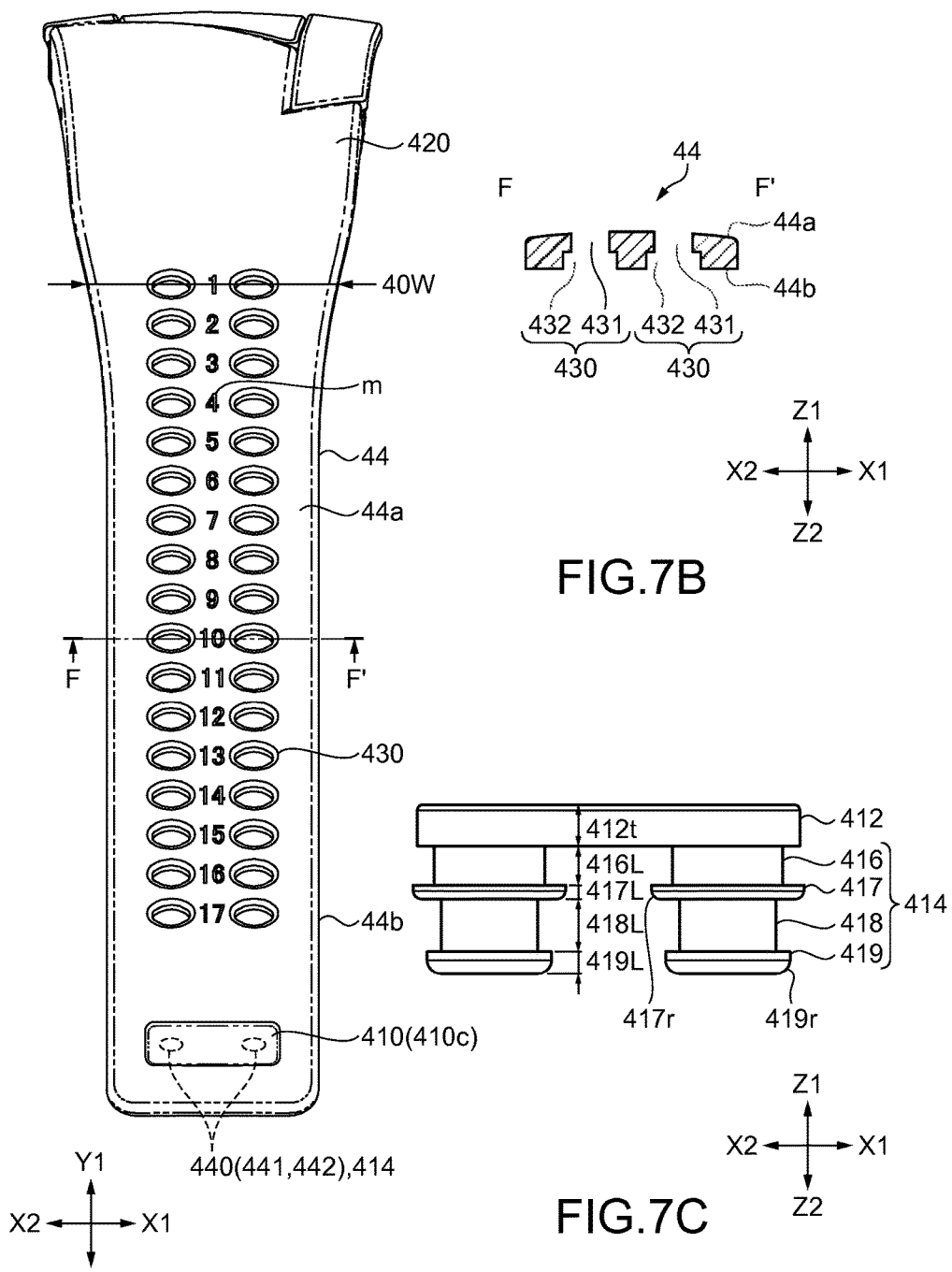

BIOLOGICAL INFORMATION MEASUREMENT DEVICE

CROSS REFERENCE TO RELATED APPLICATIONS

The present application is based on and claims priority from Japanese Patent Application No. 2013-213480, filed Oct. 11, 2013, the disclosure of which is incorporated herein by reference.

BACKGROUND

1. Technical Field

The present invention relates to a biological information measurement device which is worn by a user so as to measure biological information, such as the user's heart rate.

2. Related Art

A wrist-worn heart rate monitor generally includes a device main body, which contains the necessary electronics, and a wrist band which secures the monitor to the user's wrist. It is necessary to bring the device main body into close contact with the user's skin, such as with a tightly worn elastic band which secures the monitor tightly around the wrist. Such a heart rate monitor is disclosed in JP-A-2012-90975, which is incorporated herein by reference.

The heart rate monitor described in JP-A-2012-90975 is provided with first and second band members which are mounted on a device main body, and a connecting member. Each band member has a stretchable portion which expands and contracts along a longitudinal direction. The monitor also includes a power supply, such as a rechargeable battery, which drives the necessary electronic components.

When the biological information is detected frequently, the battery life suffers. A large display screen further drains the battery rather quickly. A larger battery is bulky and heavy, leading to fatigue in the user. An excessively heavy batter also may adversely affect the biological information measurement at the time of motion.

SUMMARY

A biological information measurement device includes a device main body which includes a sensor, a processor, and a battery. The sensor acquires biological information of a user. The processor instructs the sensor to acquire the information at certain discrete times with a period, and processes the information. The battery supplies power to the sensor and the processor. The period is selected based on the biological information.

The processor may have several modes, each of which is associated with a different period. For example, a sleeping mode in which the user is asleep may have a first period. A light work mode in which the user is awake may have a second period shorter than the first period. An active mode in which the user is awake and in motion may have a third period shorter than the second period.

The biological information may be a quantitative number, such as a pulse rate of the user. The period may be selected based on the number and/or a rate of change of the number.

The battery may be a rechargeable battery, and may be charged to an amount of charge that depends on the number of discrete times at which the information was acquired after the previous charge.

The period may be further selected based on the remaining amount of charge of the battery.

The battery may have a charge capacity sufficient for the device to obtain the information for ten hours or more without the battery needing to be recharged. The device main body may weigh less than or equal to 60 g, have a volume less than or equal to 50 cm$^3$, and/or have a thickness less than or equal to 16 mm.

BRIEF DESCRIPTION OF THE DRAWINGS

The invention will be described with reference to the accompanying drawings, wherein like numbers reference like elements.

FIGS. 7A to 7C are a plan view and a cross-sectional view schematically showing a second band portion.

DESCRIPTION OF EXEMPLARY EMBODIMENTS

Hereinafter, an exemplary embodiment of the invention will be described using the drawings, which are not necessarily to scale. To the extent that relative sizes and/or shapes of components are considered relevant, these will be explicitly mentioned in the description.

Schematic Configuration of Biological Information Measurement Device 1

Figure 1:
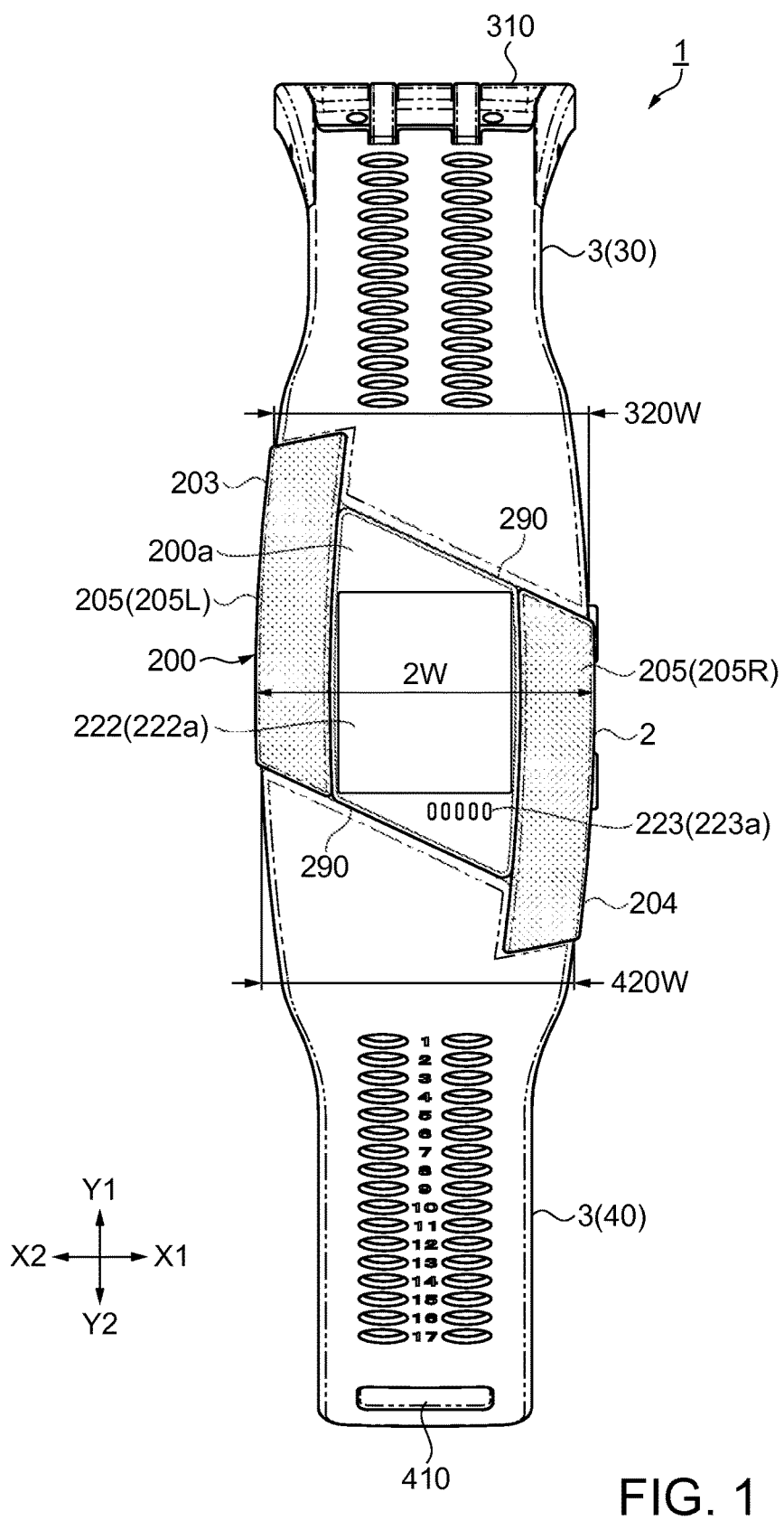
FIG. 1 is a top view schematically showing the external appearance of a biological information measurement device according to an embodiment.
Figures 2A, 2B:
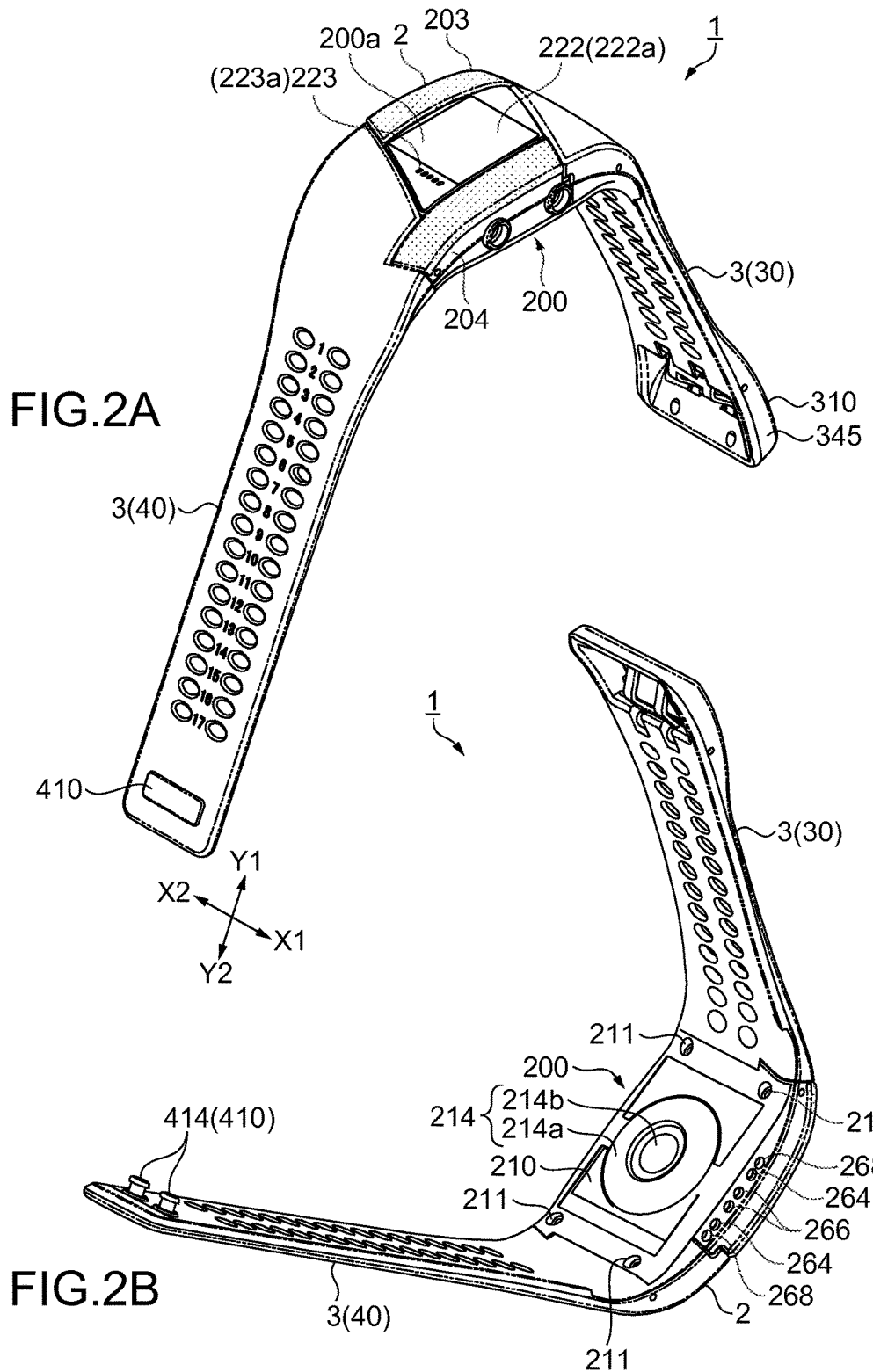
FIGS. 2A and 2B are perspective views schematically showing the external appearance of the biological information measurement device according to the embodiment.

A biological information measurement device 1 is an electronic device which can be worn on the wrist or other body part of a user to measure biological information of the user, such as the pulse rate. The measurement device 1 generally resembles a wristwatch, as shown in FIGS. 1, 2A, and 2B. The measurement device 1 includes a device main body 2 which includes the electronics and measures the biological information by contacting the user's skin, and a band 3 which is mounted on the device main body 2 and serves to attach the device 1 to the user's wrist or other body part.

Configuration of Device Main Body 2

Figure 3:
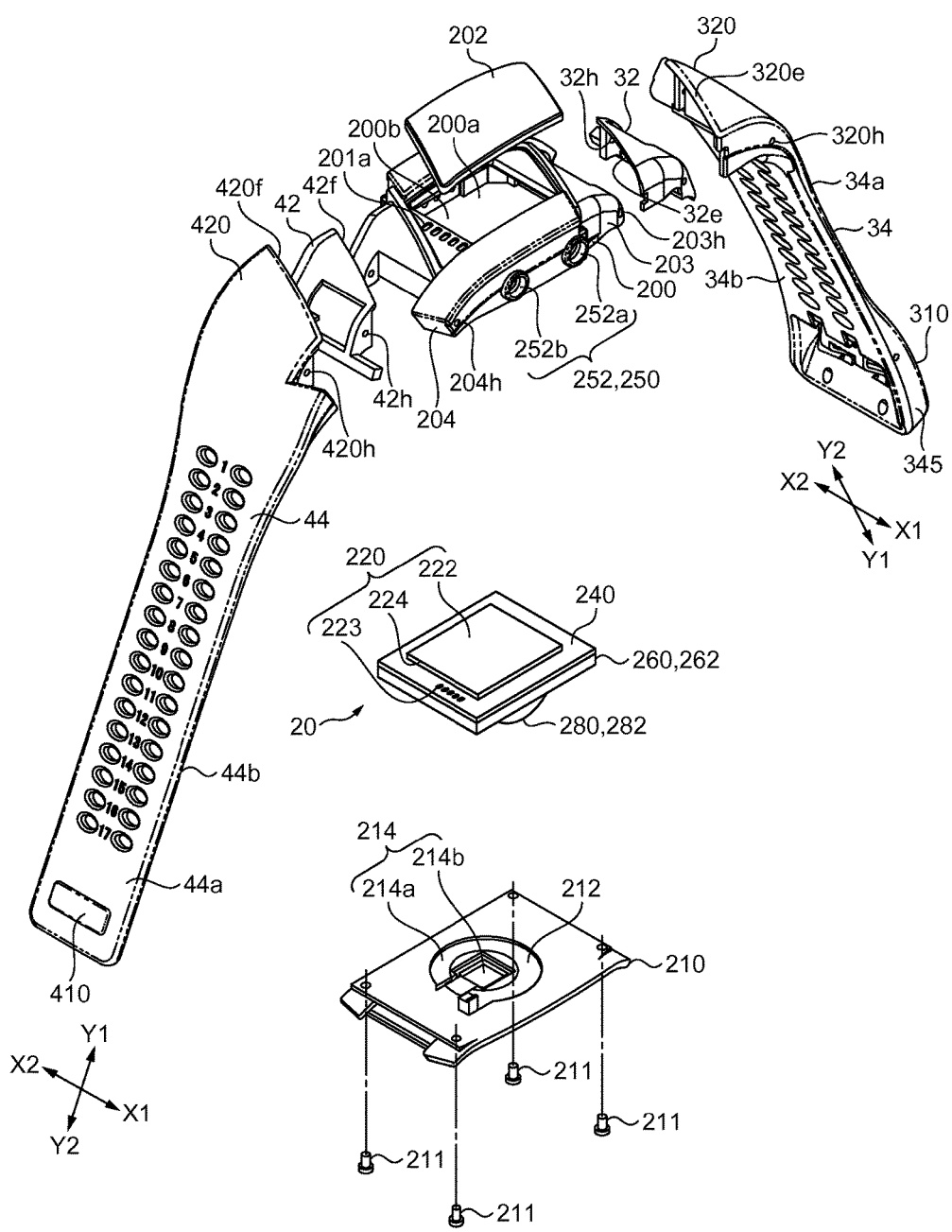
FIG. 3 is a development view schematically showing the structure of the biological information measurement device according to the embodiment.

As shown in FIGS. 2A, 2B, and 3, the device main body 2 of the measurement device 1 is provided with a module 20 (FIG. 3), and a case 200 in which the module 20 is accommodated. The module 20 is provided with a display section 220, a processing section 240, a power supply section 260, and a sensor section 280.

In addition, the display section 220 is provided with a first display portion 222 and a second display portion 223. Further, the device main body 2 is provided with an operation section 250 connected to the processing section 240, and a communication terminal 266. In addition, the device main body 2 is provided with a battery 262 connected to the power supply section 260, and a charging terminal 264 which is used to charge the battery 262.

In the case 200, a concave portion 200b in which the module 20 is accommodated is formed on the lid section 210 side thereof. The module 20 is accommodated in the concave portion 200b and the lid section 210 covers the concave portion 200b and is fixed by setscrews 211. Materials of the case 200 and the lid section 210 are not particularly limited. As an example thereof, nylon-based synthetic resin (plastic resin) may be used.

The lid section 210 has a concave shape facing the concave portion 200b. The depth of the concave portion 200b is selected according to the thickness of the battery 262 (described later).

In a presently preferred embodiment, the thickness of the device main body 2 is approximately 14 mm. When the device main body 2 is thin, the user feels less pressure. Further, it is less likely to be caught in the user's clothes. The device main body 2 should be at least approximately 8 mm thick, to ensure sufficient strength, and no thicker than approximately 16 mm to avoid being caught in the user's clothes and minimize a feeling of pressure. The lid section 210 has a concave shape thick enough to accommodate the thickness of the battery 262.

The volume of the device main body 2 depends on the shape of the lid section 210. In a presently preferred embodiment, the volume of the device main body 2 is 21 cm$^3$ and the device main body 2 is 14 mm thick. The device main body 2 should be at least approximately 15 cm$^3$, to ensure sufficient strength, and no larger than approximately 50 cm$^3$ to avoid being caught in the user's clothes and minimize a feeling of pressure.

As shown in FIGS. 2A, 2B, and 3, in the case 200, a display window 200a is provided on the opposite side to the side on which the lid section 210 is provided. The display window 200a is configured such that the user's pulse rate or the like which is displayed on the display section 220 is visible through the window 200a.

The display window 200a is provided with a first display window 222a corresponding to a first display portion 222, and a second display window 223a corresponding to a second display portion 223. The first display portion 222 is fitted into the first display window 222a (refer to FIGS. 1, 2A, 2B, and 4). Further, the second display portion 223 is fitted into the second display window 223a (refer to FIGS. 1, 2A, 2B, and 4).

Figure 4:
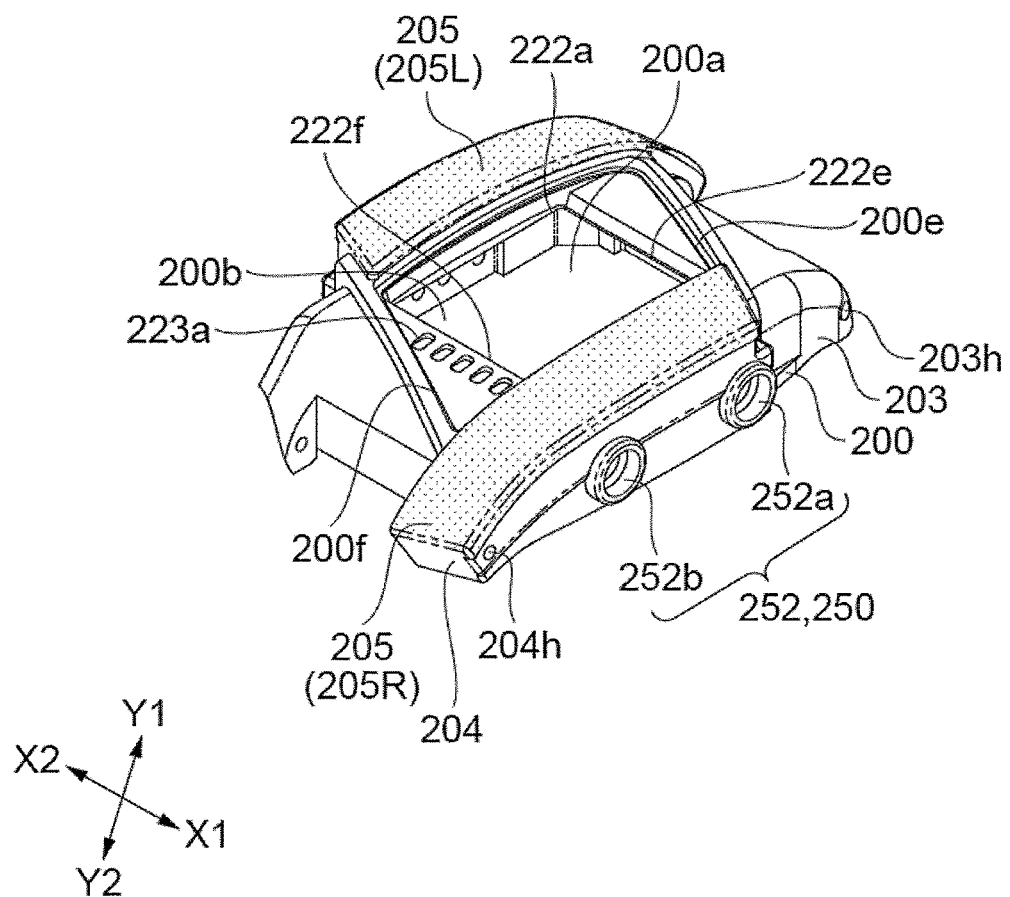
FIG. 4 is an enlarged view schematically showing the structure of a main body section of the biological information measurement device.

As shown in FIG. 4, the display window 200a has a non-rectangular parallelogram shape with two longitudinal edges disposed along the longitudinal direction of the device, and two oblique edges 200e, 200f disposed along an oblique direction that is transverse to, but not perpendicular to, the longitudinal direction.

The first display window 222a in which the first display portion 222 is fitted has a rectangular shape having sides 222e and 222f which extend in the lateral direction perpendicular to the longitudinal direction.

The second display window 223a in which the second display portion 223 is fitted has several parallel sub-windows, each with a corner-rounded rectangular shape aligned in the longitudinal direction.

The edge 200e of the display window 200a and the edge 222e of the first display window 222a define an acute angle therebetween. Further, the edge 200f of the display window 200a and the edge 222f of the first display window 222a define and acute angle therebetween.

The second display window 223a is disposed in the triangular region between the edge 200f of the display window 200a and the edge 222f of the first display window 222a.

The second display portions 223 display an operating state or the like of the measurement device 1 in a plurality of ways. Further, it is possible to make the first display portion 222 (the first display window 222a) appear larger than it actually is. Therefore, it is possible to suppress a feeling of pressure which is given to a person with the measurement device 1 mounted thereon.

Further, a display section cover body 202 formed of transparent resin, transparent glass, or the like is fitted into the display window 200a. The display section 220 is protected by the display section cover body 202. The display section cover body 202 has a non-rectangular parallelogram shape, sized to be set in the display window 200a.

As shown in FIGS. 1 to 4, at the case 200, a frame section 205 is provided along the display window 200a.

In the frame section 205, a frame portion 205R is provided in an X1 direction (the three o'clock direction when comparing the device to a wristwatch), and a frame portion 205L is provided in an X2 direction (the nine o'clock direction).

Each frame portion 205R, 205L is shaped as an isosceles trapezoid with the bases disposed in the longitudinal direction, i.e. parallel to the edges of the band 3.

In the frame portion 205L, one of the legs of the trapezoid disposed in a Y2 direction is provided as an extension of the oblique line of the edge 200f of the display window 200a, and the other leg provided in a Y1 direction is provided further to the Y1 side (twelve o'clock) than an extension of the oblique line of the edge 200e of the display window 200a.

In the frame portion 205R, one of the legs of the trapezoid disposed in the Y1 direction is provided as an extension of the oblique line of the edge 200e of the display window 200a, and the other leg provided in the Y2 direction is provided further to the Y2 side (six o'clock) than an extension of the oblique line of the edge 200f of the display window 200a.

At the frame section 205, a film 205a which includes metal is provided on the front side of the case 200 in which the display window 200a is provided. The film 205a is electrically connected to the processing section 240 (described later). The film 205a can be used as an antenna when performing wireless communication with an information processing device such as the user's computer or mobile phone (not shown) provided outside the measurement device 1. Further, the film 205a can be a capacitance type touch sensor and used as the operation section 250 (described later). In addition, the film 205a adds to the strength of the case 200 and allows the wall thickness of the case 200 to be thinner. Therefore, it is possible to keep the weight of the case 200 down.

The material of the film 205a is not particularly limited. In presently preferred embodiments, the material is capable of acting as an antenna and/or detecting a change in capacitance. In a particularly presently preferred embodiment, a material which includes nickel (Ni) is used. Nickel acts as an antenna, strengthens the case 200, acts as a touch switch, and has an attractive glossy color. In addition, a presently preferred embodiment, in order to increase performance as an antenna, the strength of the case 200, and the aesthetics, the film 205a is also provided on the side surface of the frame section 205.

As shown in FIG. 3, the display section 220 is part of the module 20 accommodated in the case 200. The first display portion 222 and the second display portion 223 are portions of the display section 220.

In the first display portion 222, biological information such as the number of pulses (i.e. heart beats), time information such as the current time, or the like is displayed depending on a selected display mode. Further, at the first display portion 222, a backlight 224 is provided and can illuminate the first display portion 222.

The first display portion 222 can include any suitable hardware capable of displaying biological information (such as a numeral or a graph configured by a dot matrix) such as the pulse rate. A liquid crystal display device is one example. Further, the backlight 224 can be any suitable light of any color. One example is an electro-luminescence (EL) panel which emits green light. It is presently preferred that the first display portion 222 is a liquid crystal panel or a light-emitting diode. This leads to good battery life.

The second display portion 223 can be any suitable light of any color capable of indicating the operation mode or the like of the measurement device 1 with its color, on/off state, or blinking. One example is a light-emitting diode, or, as illustrated, several light-emitting diodes.

As shown in FIG. 3, the processing section 240 is provided in the module 20 accommodated in the case 200.

The processing section 240 includes a substrate configured as a semiconductor device such as a microcomputer or a storage device, and an electronic circuit or the like which communicates information, and the charging control of the battery 262 connected to the power supply section 260. The display section 220, the operation section 250, the power supply section 260, the sensor section 280, and the film 205a of the frame section 205 are connected to the processing section 240. The processing section 240 processes the driving of the sensor section 280 or a signal received from the sensor section 280 (e.g. the pulse rate or another signal derived from the pulse rate) so that the pulse rate or other biological information can be displayed in the display section 220.

Further, the processing section 240 stores of biological information and communicates with the information processing device provided outside the measurement device 1, thereby outputting the stored data.

As shown in FIG. 3, the operation section 250 providing a command to the processing section 240 is provided in the module 20 accommodated in the case 200.

The operation section 250 includes a button 252 configured to be pressed by the user, Pressing the operation button 252 may. e.g. switch between modes, such as a pulse measurement mode of displaying pulse rate; a clock mode of displaying the current time, a stopwatch time, or the like; a remaining battery level display mode; a setting mode of setting an interval of detecting the pulse or the charging capacity of the battery 262; a lighting mode of the backlight 224 of the display section 220; or the like.

The operation section 250 is provided in the side surface of the case 200 in the X1 direction (the three o'clock-side direction) shown in FIGS. 1 to 4. The operation section 250 can be provided with a plurality of operation buttons 252. It is presently preferred that at least one operation button 252 is provided on the extension line of the edge 200e of the display window 200a. In this way, the user visually recognizes the edge 200e of the display window 200a, whereby it is possible to easily grasp the position where the operation button 252 is provided, and thus it is possible to prevent an erroneous operation.

In a further presently preferred embodiment, pressing all the buttons 252 at substantially the same time switches to a setting mode to allow the user to set the measurement device 1. In the illustrated embodiment, two buttons 252a and 252b are provided. The button 252a can be pressed by an index finger and adding a force associated with the pressing to the case 200 through a thumb.

The button 252b can be pressed by a ring finger and adding a force associated with the pressing to the case 200 through a thumb. Therefore, it is preferable that an interval at which the operation buttons 252a and 252b are provided is an interval in which fingers (for example, a thumb and an index finger, or a thumb and a ring finger) performing the operation do not overlap, in a range that the fingers performing the operation reach.

As shown in FIG. 3, the power supply section 260 is provided in the case section 200. The rechargeable battery 262 is provided in the power supply section 260. A small and lightweight battery with a high storage density is preferable. Examples are a lithium-ion polymer battery and a lithium-ion battery.

The charging terminal 264 and the communication terminal 266 are provided in the side surface of the case 200 in the X2 direction (the nine o'clock direction). Each of the charging terminal 264 and the communication terminal 266 is provided as a single terminal or as a plurality of terminals, depending on design considerations. In the illustrated example, two charging terminals 264 and two communication terminals 266 are provided.

In the illustrated example, the communication terminals 266 are provided between the charging terminals 264. In other words, the charging terminal 264 is disposed outside the communication terminal 266 (in the Y direction shown in FIG. 5B). In addition, a positioning hole 268 for a connector (not shown) to be connected to the charging terminal 264 and the communication terminal 266 is provided outside each charging terminal 264 (in the opposite Y direction). In addition, the charging terminal 264 and the communication terminal 266 protrude from the side surface of the case 200, while the positioning hole 268 is a blind hole.

Figure 5A:
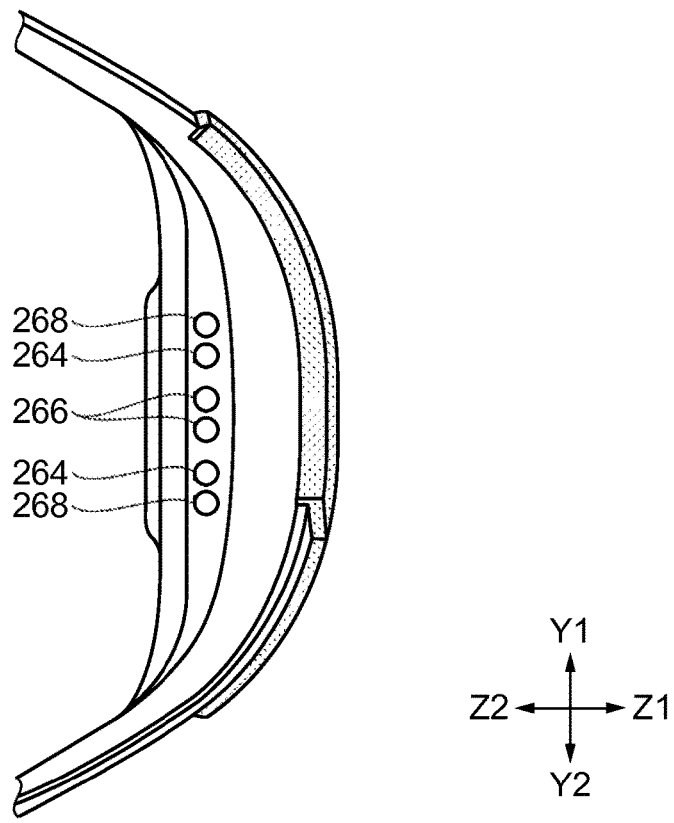
FIGS. 5A and 5B are side views schematically showing the nine o'clock-side side surface of the main body section of the biological information measurement device.
Figure 5B:
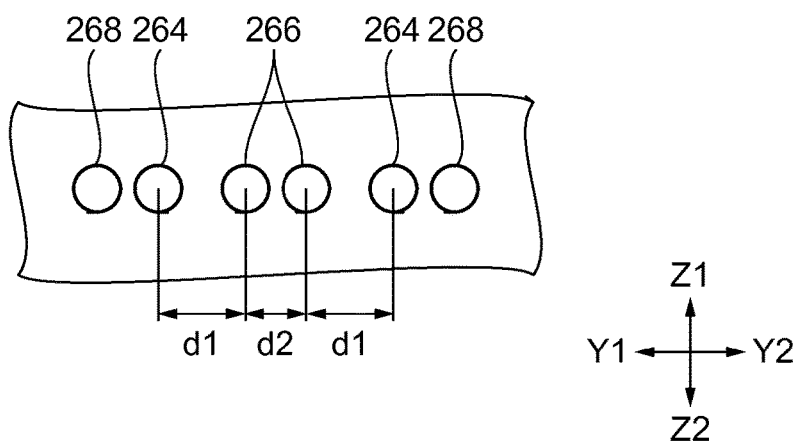

As shown in FIG. 5B, a distance d1 between each charging terminal 264 and the closest communication terminal 266 is wider than a distance d2 between the two communication terminals 266. In this way, it is possible to avoid short circuits between the charging terminals 264 and between the charging terminal 264 and the communication terminal 266.

As for the charging terminal 264 and the communication terminal 266, it is possible to use a material having electric conductivity, such as stainless steel, which is corrosion resistant. Further, since the charging terminal 264 and the communication terminal 266 protrude from the case 200 (such as with a convex lens-shaped convex curved surface), thus minimizing corrosion and maintaining electric conductivity. Further, the charging terminal 264 and the communication terminal 266 are provided in the side opposite the operation section 250, and therefore, the fingers operating the operation buttons 252a and 252b do not usually touch the terminals, thereby preventing contamination due to sebum or the like. In addition, the surfaces of the charging terminal 264 and the communication terminal 266 may be plated with a conductive material having corrosion resistance, for example, gold or the like, to further improve the corrosion resistance.

Returning to FIG. 3, the sensor section 280 will be described.

As shown in FIG. 3, the sensor section 280 provided with a sensor unit 282 is provided in the module 20 accommodated in the case 200. Any suitable sensor unit capable of measuring biological information, such as a pulse rate, may be used. One exemplary sensor will be described. The sensor unit 282 is a light sensor and is provided with a sensor case, and a sensor substrate with a light emitting element and a light receiving element mounted thereon. The sensor unit 282 irradiates light toward the wrist of the user from the light emitting element such as a light emitting diode (LED) and receives the light reflected by a blood vessel of the wrist by the light receiving element such as a photodiode. Such a sensor is described in detail in the present assignee's co-pending application Ser. No. 14/463,519, titled "Physiological Information Measuring Apparatus," filed Aug. 19, 2014, which is hereby incorporated by reference.

A sensor bank portion 212 in which the sensor section 280 is accommodated is provided at the lid section 210. At least a portion of the sensor section 280 is provided on the sensor bank portion 212 having a disk shape recessed into the lid section 210 in the direction toward the user's skin. The sensor bank portion 212 is provided with a sensor convex portion 214 (refer to FIG. 2B).

The sensor convex portion 214 is provided so as to be pressed against the wrist or the like of the user with the measurement device 1 mounted thereon. The sensor convex portion 214 is provided with a base portion 214a extending from the lid section 210, and a tip portion 214b which is pressed against the user's skin.

It is preferable that the base portion 214a of the sensor convex portion 214 is made of an opaque material and the tip portion 214b is made of a transparent or translucent material. Further, it is preferable that the tip portion 214b has a shape which avoids irregular reflection of the light and in which the user does not feel pain at the time of putting on the device.

Therefore, in some embodiments, the base portion 214a is made of the same synthetic resin as the lid section 210 but has light-shielding coloring applied thereto. Further, the tip portion 214b is preferable arc shaped and made of transparent glass or transparent acrylic resin.

Configuration of Band 3

The configuration of the band 3 will be described using FIGS. 1 to 3, 6A, and 6B.

The band 3 is provided in order to mount the device main body 2 on the user. The band 3 has two portions: one at each end of the device main body 2, as shown in FIGS. 1, 2A, and 2B. The first band portion 30 is mounted on a lug 203 (at the twelve o'clock side) of the device main body 2 by a mounting member 32, as shown in FIG. 3. Further, the second band portion 40 is mounted on a lug 204 (at the six o'clock side) of the device main body 2 by a mounting member 42.

A connection portion 310 which removably connects the first band portion 30 and the second band portion 40 is provided at an end of the first band portion 30 opposite the device main body 2. Further, a hook 410 which secures the second band portion 40 to the first band portion 30 is provided at an end of the second band portion 40 opposite the device main body 2.

In the following description, in the first band portion 30, the device main body 2 is described as being attached to the first end, and the side on which the connection portion 310 is provided is the second end. Similarly, in the second band portion 40, the device main body 2 side is the first end and the hook 410 is attached to the second end.

Configuration of First Band Portion and Second Band Portion

Figures 6A, 6B:
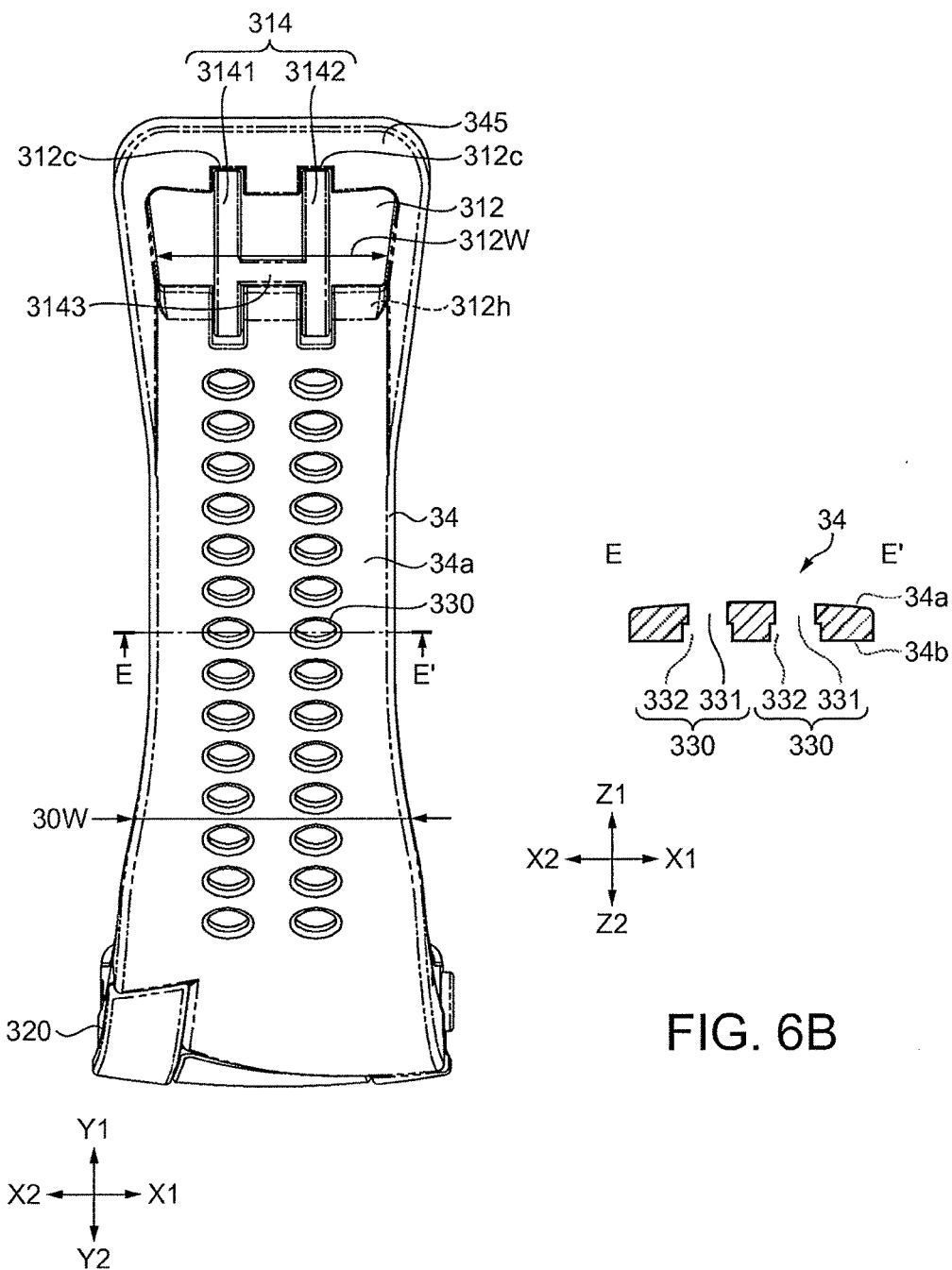
FIGS. 6A and 6B are a plan view and a cross-sectional view schematically showing a first band portion.

The first band portion 30 shown in FIGS. 3, 6A, and 6B has a belt portion 34, a cover portion 320 as an additional connection portion provided on the first end of the belt portion 34, and the previously mentioned connection portion 310 on the second end. The second band portion 40 shown in FIGS. 3, and 7A to 7C has the belt portion 44, the cover portion 420 as a further connection portion provided at the first end of the belt portion 44, and the hook 410 on the second end. FIG. 7A also shows a concave portion 410c in which the hook 410 is provided and a hole portion 440.

In the following description, the surface contacting the user's wrist is referred to as a back surface 34b of the belt portion 34 and a back surface 44b of the belt portion 44. The opposite, visible surface is referred to as a front surface 34a of the belt portion 34 and a front surface 44a of the belt portion 44.

Mounting on Device Main Body 2

The first band portion 30 and second band portion 40 are mounted on the device main body 2 such that the cover portions 320, 420 cover the lugs 203, 204, respectively, with the mounting member 32, 42 sandwiched between the lug 203, 204 and the cover portion 320, 420, respectively.

The cover portions 320, 420 and the lugs 203, 204 are pivotally supported by inserting respective spring rods (not shown) into respective holes 32h, 42h provided in the mounting members 32, 42 and rod holes 203h, 204h provided in the lugs 203, 204 and locking both ends of each spring rod to locking holes 320h, 420h provided in the cover portions 320, 420, respectively.

In the illustrated embodiment, the connection between the device main body 2 and the first band portion 30 is performed with a miter joint such that the edge 202e of the display section cover body 202 faces the end portions 320e and 32e, which are ends of the cover portion 320 and the mounting member 32, respectively, such that the mounting member 32 and the cover portion 320 contact the edge 200e of the display window 200a. The connection between the device main body 2 and the second band portion 40 is performed with a miter joint such that the edge 202f of the display section cover body 202 faces the end portions 420f and 42f, which are ends of the cover portion 420 and the mounting member 42, respectively, such that the mounting member 42 and the cover portion 420 contact the edge 202f of the display window 200a.

Further, in the measurement device 1, a bottomed groove (i.e. a blind groove) 290 is provided between the first band portion 30 and the device main body 2 to prevent wear due to the contact of the case 200 with the mounting member 32 and the cover portion 320 when the belt portion 34 expands or contracts. An additional bottomed groove 290 is provided between the second band portion 40 and the device main body 2 to prevent wear due to the contact of the case 200 with the mounting member 42 and the cover portion 420 when the belt portion 44 expands or contracts.

Belt Portions 34, 44

The belt portions 34, 44 are highly elastic in order to tightly mount the device main body 2 against the wrist or the like of the user. The belt portions 34, 44 may be made using a material which includes polyurethane resin or silicone resin, thereby having the stretchability and flexibility of these materials.

The belt portions 34, 44 each has a thickness in the Z direction of a central portion in a direction of a width 30W, 40W increased in a cross-section in the X direction, along line E-E' in FIG. 6A and line F-F' in FIG. 7A, whereby strength during expansion and contraction and during flexion are secured.

A hole 330 (in which the hook 410 of the second band portion 40 is secured) is provided in the belt portion 34. A hole 430 (in which the projecting bar 314 of the first band portion 30 is secured) is provided in the belt portion 44. The holes 330, 430 are provided in parallel in rows in the Y direction.

In each hole 330, 430, as shown in FIGS. 6B and 7B, a hole portion 331, 431 on the front side and a hole portion 332, 432 on the back side are coaxial.

The holes 330, 430 each has an elliptical shape having a major diameter in the X direction and a minor diameter in the Y direction. Both the major diameter and the minor diameter are longer in the hole portions 332, 432 than in the respective hole portions 331, 431.

In addition, the shape of the holes 431 and 432 depends on the cross-sectional shape of the projecting bar 314. In the illustrated embodiment, the holes 431 and 432 are elliptical, thereby being able to be easily deformed, and thus the insertion of the projecting bar 314 can be easily performed. In addition, the holes 431 and 432 also have an excellent restoring force after the deformation.

As shown in FIG. 7A, numerical symbols m are provided between the rows of hole portions 430. The values of the symbols m increase in the Y2 direction. The symbols m are, e.g. numbers 1-17, as illustrated, or a-q. The latter may sometimes be preferred because the tenth plus symbols do not take up any more room than the first through ninth, unlike with numbers.

The symbols m allow the user to identify his or her unique optimum position for inserting the projecting bar 314 at a glance. Further, the symbol m is positioned between rows of hole portions 430, and therefore, additional space is not necessary.

As shown in FIG. 7A, the belot portion 44 further includes a concave portion 400c in which a base portion 412 of the hook 410 is fitted. The belot portion 44 also includes the hole portion 440 in which a pin 414 extending from the base portion 412 is inserted.

The concave portion 400c has a concave shape conforming to an outer peripheral edge of the base portion 412 on the front surface 44a of the belt portion. Further, a depth 400d of the concave portion 400c is approximately the same dimension as a thickness 412t of the base portion 412.

The hole portions 440 are provided in parallel in the X direction and coaxially with the pins 414 extending from the base portion 412, as shown in FIG. 7A. In the hole portion 440, a hole (not shown) provided in a bottom portion of the concave portion 400c on the front surface 44a and a hole (not shown) in the back surface 44b are coaxial.

Connection Portion 310

The connection portion 310 is provided on the second end of the belt portion 34.

A thick portion 345 whose thickness is higher than at a portion in which the holes 330 are provided is provided at the second end of the belt portion 34. The connection portion 310 is provided at the thick portion 345. An insertion hole 312 into which the second band portion 40 is inserted and a projecting bar 314 which is inserted into a hole portion 430 (refer to FIGS. 7A to 7C) provided in the second band portion 40 are provided at the connection portion 310.

The band insertion hole 312 has a width 312W in the X direction which is wider than a width 40W (refer to FIG. 7A) of the second band portion 40.

Further, the width 312W is tapered, and is wider at the Y1 side than the Y2 side.

It is therefore possible to easily insert the second band portion 40 in the Y1 side of the insertion hole 312. Further, it is possible to tighten the band by pulling the second band portion 40 to the Y2 side.

The projecting bar 314 is pivotally supported on the belt portion 34 by a spring rod (not shown) which is inserted into the locking hole 312h at the Y2 side of the band insertion hole 312, and a hole (not shown) in the projecting bar 314. A portion of the projecting bar 314 is fitted into the concave portion 312c at the Y1 side of the band insertion hole 312, whereby the projecting bar 314 is locked to the belt portion 34.

Two bar portions 3141 and 3142 extend in the Y1 direction from the projecting bar 314. A connection bar 3143 extends in the X direction. The cross-sectional shape of each of the bar portions 3141 and 3142 is flat. The projecting bar 314 has a flat shape, whereby it is possible to increase a contact area when having been inserted into the hole portion 430, prevent the hole portion 430 from being extended, and prevent a shift of the measurement device 1 when worn by the user. Thus, the projecting bar 314 has an H-shape, and thus it is possible to easily insert the projecting bar 314 into the hole portions 430, while maintaining an interval between the bar portions 3141 and 3142 by the connection bar 3143.

The material of the projecting bar 314 is not particularly limited, but it should have toughness capable of withstanding the restoring forces of the belt portions 34 and 44, and corrosion resistance. Stainless steel is one example. Further, the projecting bar 314 is subjected to hairline machining along the Y direction to increase is visibility, thereby aiding insertion into the hole portion 430.

Hook 410

As shown in FIGS. 1 to 3 and FIGS. 7A to 7C, the hook 410 is provided on the second end of the belt portion 44.

As shown in FIG. 7C, the hook 410 is provided with the base portion 412 and the pins 414 extending from the base portion 412. The pin 414 includes a first shaft 416 and a second shaft 418. The hook 410 locks the second band portion 40 to the first band portion 30 by inserting the pins 414 into the holes 330 of the first band portion 30.

The pins 414 are spaced apart at the same interval as the holes 330 of the belt portion 34 in the X direction, and the cross-sectional shape is elliptical to match the shape of the hole 440, i.e. has a major diameter in the X direction and a minor diameter in the Y direction.

The first shaft portion 416 protrudes from the base portion 412 at the X1 end and the second shaft portion 418 protrudes from the base portion 412 at the X2 end.

A first shoulder 417 is provided on the first shaft portion 416 in the Z2 direction from the base portion 412. The first shoulder 417 has a curved surface 417r at the Z2 edge.

The cross-sectional area of the first shoulder 417 is larger than that of the first shaft portion 416, larger than the hole 441, and smaller than the hole 442.

Further, a second shoulder 419 is provided on the second shaft portion 418 in the Z2 direction from the first shaft portion 416. The second shoulder 419 has a curved surface 419r at the Z2 edge.

The cross-sectional area of the second shoulder 419 is larger than that of the second shaft portion 418, larger than the hole 331, and smaller than the hole 332.

The thickness in the Z direction of the base portion 412 and the length in the Z direction of the pin 414 are determined depending on the depths of the hole portion 440 and the hole 331 (the hole 330).

The thickness 412*t* of the base portion 412 is approximately the same as the depth of the concave portion 400*c*. A length 416L of the first shaft portion 416 is approximately the same as the depth of the hole 441. The thickness 417L of the first shoulder 417 is approximately the same as the depth of the hole 442. The length 418L of the second shaft portion 418 is approximately the same as the depth of the hole 331. The length 419L of the second shoulder 419 is approximately the same as the depth of the hole 332.

The base portion 412 is fitted into the concave portion 410*c*. In addition, the pins 414 are inserted into the hole portions 440. The second shaft portions 418 protrude from the back surface 44*b* of the belt portion 44, thereby being able to be inserted into the holes 330 in the first band portion 30.

In this way, in the first shaft portion 416 inserted into the hole 441, the first shoulder 417 is caught in the hole 441, and thus the hook 410 is secured to the belt portion 44.

More specifically, due to the curved surface 417*r* of the first shoulder 417, contact resistance when inserting the first shaft portion 416 into the hole 441 is low. In addition, the curved surface 417*r* is not provided at the first shoulder 417 on the base portion 412 side, and therefore, when extracting the first shaft portion 416 from the hole 441, a larger force than the force at the time of insertion is required. Therefore, the hook 410 is secured to the belt portion 44 until the user purposely removes it.

Further, the second shoulder 419 is caught in the hole 331 in the first band portion 30, thus securing the second band portion 40 to the first band portion 30.

More specifically, due to the curved surface 419*r* of the second shoulder 419, contact resistance when inserting the second shaft portion 418 into the hole 331 is low. In addition, the curved surface 419*r* is not provided at the second shoulder 419 on the first shaft portion 416 side, and therefore, when extracting the second shaft portion 418 from the hole 331, a larger force than the force at the time of insertion is required. Therefore, the second band portion 40 is secured to the first band portion 30 until the user purposely removes it.

Cover Portions 320, 420

The cover portion 320 is disposed at the Y2 side of the belt portion 34, and has the locking hole 320*h* provided therein. The cover portion 420 is disposed on the Y1 side of the belt portion 44, and has the locking hole 420*h* provided therein.

The cover portion 320 connects the first band portion 30 to the device main body 2 through the mounting member 32. The cover portion 420 connects the second band portion 40 to the device main body 2 through the mounting member 42. A width 320W of the cover portion 320, a width 420W of the cover portion 420, and a width 2W of the device main body 2 are all approximately equal (in the X direction).

Further, the cover portion 320 has the oblique end portion 320*e* which parallels the edge 200*e* of the non-rectangular parallelogram shaped display window 200*a* (refer to FIG. 3). The cover portion 420 has the oblique end portion 420*f* which parallels the edge 200*f* of the display window 200*a*. In this way, the device main body 2, the first band portion 30, and the second band portion 40 appear integrally formed, and thus it is possible to alleviate a feeling of pressure due to mounting. Further, since the device main body 2 does not protrude from the band portions 30, 40 in the width direction (the X direction), the clothes of the user are prevented from being caught on the device main body 2 at the time of putting on the apparatus.

Operation of Device Main Body 2

The sensor section 280 of the device main body 2 can detect biological information of the user, e.g. the pulse rate. The biological information can be measured intermittently.

The biological information is transmitted from the sensor unit 282 to the processing section 240 and various information processing is performed thereon. Additionally or alternatively, the biological information is displayed on the display section 220 and/or recorded in a storage device provided in the processing section 240. The recorded biological information can be transmitted to outside of the device main body 2 by wireless communication between the device main body 2 and a receiving device (not shown) of the measurement device 1, or by wired communication through the communication terminal 266.

Taking the pulse rate as exemplary biological information, it will be appreciated that both the pulse rate and the rate of change of the pulse rate over time are significantly different depending on the user's activity. For example, when the user is sleeping, the rate of change is small. On the other hand, when the user is in motion (walking, jogging, or the like), the rate of change is large.

It is important to catch significant changes in pulse rate. Therefore, even if the pulse rate is detected continuously when the pulse rate is substantially constant, the information gleaned is not particularly useful. However, if it were detected intermittently during periods of abrupt change, it is not possible to closely monitor the change, and thus useful biological information is not obtained.

Constant continuous measurements would ensure that relevant information is always captured, but the battery 262 would be quickly consumed, at which point the information could no longer be measured.

Therefore, the frequency at which the pulse rate is measured can be changed depending on the detected pulse rate. In other words, when the rate of change is small, a detection interval is long, and when the rate of change is large, a detection interval is shorter.

Specifically, when the pulse is less than a certain value (for example, a typical resting pulse rate, e.g. 70 bpm) and the rate of change is in a certain range, the detection period is increased. When the pulse exceeds the certain value and/or the rate of change is high, the detection period is shortened.

The measurement device may be switchable between several modes, e.g. continuously measuring the biological information, displaying time of day or stopwatch time on the display section 220 without measuring the biological information, and displaying nothing without measuring the biological information.

By analyzing the biological information, the device can assign an appropriate detection period needed for, for example, one day (24 hours). or to break the day up according to activity such as a daytime activity zone or a night-time sleeping zone, for example.

The appropriate detection period will be different for each individual user. Therefore, it is possible for the user to set the period to any desired value by using the operating section 250.

Therefore, consumption of the battery 262 is slowed by not measuring too often when the rate of change of the information is small, thus extending the battery life.

Power consumption (current consumption) in the measurement device 1 according to one exemplary embodiment will be described.

When continuously measuring the pulse (at a sampling rate of 15 Hz, for example) (hereinafter referred to as a "detection mode"), current consumption is approximately 1400 µA. When displaying time or the like without measuring (including lighting of the backlight 224, and the like, hereinafter referred to as a "time display mode"), current consumption is approximately 460 µA. When not measuring, and displaying time without the back light ("standby mode"), current consumption is approximately 350 µA. When not displaying and not measuring ("non-display mode"), current consumption is approximately 14 µA.

Here, in a case where the capacity of the battery 262 (a coin type lithium-ion battery, model PD2032 is illustrated) which is installed is Typ45 (nominal 45 mA·h, i.e. 45,000 µA·h), in a case of continuing the detection mode (1400 µA), it is possible to continue it for approximately 32 hours. Further, in a case of continuing the time display mode (460 µA), it is possible to continue it for approximately 98 hours (four days). Further, in a case of continuing the standby mode (350 µA), it is possible to continue it for approximately 129 hours (five days). Further, in a case of continuing the non-display mode (14 µA), it is possible to continue it for approximately 3214 hours (more than four months).

The detection period can be selected based on the pulse and/or the rate of change, as described above.

For example, an operation of the measurement device 1 is performed at the detection mode (1400 µA) in a case where a test object is in motion. Further, the measurement device 1 operates with the ratio between the detection mode (1400 µA) and the time display mode (460 µA) being 1:1 in a case where a test object is performing light work or the like, leading to an average current of 930 µA. Further, the measurement device 1 operates with the ratio between the detection mode (1400 µA) and the standby mode (350 µA) being 1:4 when a test object is at a resting state such as sleeping, leading to an average current of 560 µA. Here, it is assumed that time when a test object is in motion is 8 hours, time when a test object is performing light work is 8 hours, and time in a resting state is 8 hours.

Energy needed in order to measure biological information associated with the activity of the user is subjected to current consumption of 11,200 mA·h for 8 hours when a test object is in motion, 7,440 mA·h for 8 hours when light work is being performed, and 4,480 mA·h for 8 hours in a resting state, a total of 23,120 mA·h, leaving plenty of charge left in the 45,000 mA·h battery. Therefore, it is possible to measure the biological information continuously for 24 hours or more on a single charge.

It is therefore possible to obtain a full day of biological information (i.e. one daytime and one sleep cycle). A 36 hour battery life allows for obtaining, e.g., daytime→sleep-→daytime. A 48 hour battery life allows for obtaining two days of data.

The operation ratio can be tailored to the individual user's habits, and optimized to obtain the longest possible battery life.

The battery life can also be optimized by selecting a battery 262 with an appropriate capacity, and selecting the number of batteries 262, preferably without the thickness of the device main body 2 exceeding 16 mm.

Further, it is possible to extend the detection period when the battery is running low.

In other words, when the processing section 240 determines that the measurement of biological information in a measurement period set in advance cannot be achieved due to the remaining capacity of the battery 262, the period is lengthened. In this way, even if the action of the user is different from the expected content set in advance, missing measurements are prevented. Therefore, it is possible to objectively analyze the lifestyle of the user by performing the measurement of biological information continuously over a long period of time.

Charging of Device Main Body 2

The battery 262 should be charged when the device main body 2 is not being worn. A connector (not shown) is connected to the charging terminal 288, and a charging control circuit, provided in the processing section 240, controls the charging.

Here, it is required that the amount of charge of the battery 262 and the capacity of the battery 262 are equal to the power (energy) amount according to the number of times of detection (a measurement period) of biological information.

For example, to measure the biological information for 24 hours, the charging of power according to the detection period for 24 hours is performed. Current consumption to measure continuously for 24 hours is approximately 33,600 µA·h (approximately 1400 µA times 24 hours). Therefore, the amount of charge of the battery 262 is set to be greater than or equal to 33,600 µA·h. Measuring only during the daytime activity time zone (8 hours) requires only 11,200 µA·h (approximately 1400 µA times 8 hours). Therefore, the amount of charge of the battery 262 is set to be greater than or equal to 11,200 µA·h. The amount of charge of the battery 262 can be controlled based on biological information analyzed in the processing section 240 and is different for each user.

In this way, the amount of charge can be only how much is needed, which shortens charging time and prevents deterioration of the battery 262.

The capacity of the battery 262 is selected according to measurement time and the detection period. For example, in a case of the aim being the measurement of biological information in an activity time zone, it is possible to select the battery 262 having a capacity according to a detection interval (the number of times of detection) needed in the activity time zone. For example, in a case of aiming at the measurement of biological information in a sleeping time zone, it is possible to select the battery 262 having a capacity according to a detection interval (the number of times of detection) needed in the sleeping time zone. That is, by varying the capacity of the battery 262 according to the times in which the measurement is desired, unnecessary weight is eliminated. In addition, by varying the size of the case section 200 of the device main body 2 according to the electrical capacity and the physical volume of the battery 262, unnecessary bulk is eliminated. In other words, the device main body 2 can be available in several different sizes and each individual user can select the size that suits his or her lifestyle and personal preferences.

According to the embodiment described above, the following effects can be obtained.

According to the measurement device 1, it is possible to measure the user's biological information by the sensor section 280 provided in the device main body 2 mounted on the user by the band 3. The biological information is intermittently detected by being controlled in the processing section 240. Therefore, power is intermittently consumed. Therefore, the amount of time until the battery becomes exhausted in increased.

What is claimed is:

1. A biological information measurement device, comprising:
    a device main body, comprising:
        a sensor configured to acquire biological information of a user;

a processor configured to instruct the sensor to acquire the information at certain discrete times with a period, and further configured to process the information; and a battery configured to supply power to the sensor and the processor;

wherein the period is selected from a group of periods comprising a first period, a second period shorter than the first period, and a third period shorter than the second period, based on the biological information and a remaining amount of charge of the battery, and wherein the processor comprises a plurality of modes, comprising at least two members selected from the group consisting of:

a sleeping mode in which it is determined that the user is asleep, wherein the period is the first period;

a light work mode in which it is determined that the user is awake, wherein the period is the second period; and an active mode in which it is determined that the user is awake and in motion, wherein the period is the third period.

2. The device of claim 1, wherein the biological information comprises a measurement of a quantitative number, and wherein the period is selected based on at least one member of the group consisting of: the number, and a rate of change of the number.

3. The device of claim 2, wherein the number is a pulse rate of the user.

4. The biological information measurement device according to claim 1, wherein the battery is a rechargeable battery, and when the battery is charged, the amount of charge to which the battery is charged is selected according to the number of discrete times at which the information was acquired after a previous charging of the battery.

5. The device of claim 1, wherein the battery has a charge capacity sufficient for the device to obtain the information for ten hours or more without the battery needing to be recharged.

6. The device of claim 5, wherein the device main body weighs less than or equal to 60 g.

7. The device of claim 5, wherein a volume of the device main body is less than or equal to 50 cm3.

8. The device of claim 5, wherein a thickness of the device main body is less than or equal to 16 mm.

9. A biological information measurement method, comprising:

acquiring biological information of a user at certain discrete times with a period; and selecting the period, from a group of periods comprising a first period, a second period shorter than the first period, and a third period shorter than the second period, based on the biological information and a remaining amount of charge of the battery, wherein the method further comprises a plurality of modes, comprising at least two members selected from the group consisting of:

a sleeping mode in which it is determined that the user is asleep, wherein the period is a first period;

a light work mode in which it is determined that the user is awake, wherein the period is the second period; and an active mode in which it is determined that the user is awake and in motion, wherein the period is the third period.

10. The method of claim 9, wherein the biological information comprises a measurement of a quantitative number, and wherein selecting the period comprises selecting the period based on at least one member of the group consisting of: the number, and a rate of change of the number.

11. The method of claim 10, wherein the number is a pulse rate of the user.

12. The method of claim 9, further comprising charging the battery to contain a charge according to the number of discrete times at which the information was acquired after a previous charging of the battery.

13. The method of claim 9, wherein acquiring the information comprises acquiring the information for ten hours or more without needing to recharge the battery.

* * * * *